US006443149B1

(12) United States Patent
Wise

(10) Patent No.: US 6,443,149 B1
(45) Date of Patent: Sep. 3, 2002

(54) CLOSED CIRCUIT ESCAPE BREATHING APPARATUS

(75) Inventor: Layton A. Wise, Washington, PA (US)

(73) Assignee: Mine Safety Appliances Company, Pittsburgh, PA (US)

( * ) Notice: Subject to any disclaimer, the term of this patent is extended or adjusted under 35 U.S.C. 154(b) by 0 days.

(21) Appl. No.: 09/263,895

(22) Filed: Mar. 5, 1999

Related U.S. Application Data

(63) Continuation-in-part of application No. PCT/US97/15672, filed on Sep. 5, 1997.
(60) Provisional application No. 60/025,617, filed on Sep. 6, 1996.

(51) Int. Cl.[7] ........................ A61M 15/00; A61M 16/00
(52) U.S. Cl. ........................... 128/202.26; 128/205.12; 128/205.17; 128/205.22; 128/205.28
(58) Field of Search ....................... 128/202.26, 204.15, 128/205.12, 205.17, 205.22, 205.28, 201.29, 202.19; 224/678, 679, 628, 629, 576

(56) References Cited

U.S. PATENT DOCUMENTS 3,111,947 A * 11/1963 Leffler, Jr. et al. .......... 128/191
3,565,068 A * 2/1971 Bickford ..................... 128/142
3,671,024 A * 6/1972 Breiling .................... 261/39 R
3,773,044 A * 11/1973 Wallace ................... 128/142.6
3,794,030 A * 2/1974 Cotabish et al. ............ 128/202
3,881,394 A * 5/1975 Netteland .................... 89/1 B
3,938,512 A * 2/1976 Mausteller et al. ..... 128/191 R
3,942,524 A * 3/1976 Li et al. ..................... 128/147
3,955,931 A * 5/1976 Thompson ................... 23/281
4,154,236 A * 5/1979 Eckstein et al. ........ 128/191 R
4,155,361 A 5/1979 Mascher
4,164,218 A * 8/1979 Martin .................... 128/142.7
4,233,971 A * 11/1980 Gronau et al. ......... 128/202.26
4,287,887 A 9/1981 Hinz et al.
4,292,967 A * 10/1981 Pasterneck ............. 128/202.26
4,297,998 A * 11/1981 Christianson .......... 128/204.26
4,409,978 A * 10/1983 Bartos ................... 128/205.12
4,459,981 A 7/1984 Mascher et al.
4,461,291 A * 7/1984 Mascher et al. ....... 128/202.26
4,491,130 A * 1/1985 Pasterneck ............. 128/202.26
4,586,500 A * 5/1986 Glynn ................... 128/204.15
4,621,964 A * 11/1986 Radtke et al. ................. 413/9
4,635,629 A * 1/1987 Thorp et al. ........... 128/202.26
4,671,270 A * 6/1987 Kato ..................... 128/202.26
4,704,778 A * 11/1987 Radtke et al. ................ 29/235
4,744,357 A * 5/1988 Bartos ................... 128/205.12
4,805,608 A * 2/1989 Eckstein et al. ....... 128/202.26
4,821,711 A 4/1989 Eckstein et al.
4,840,170 A * 6/1989 Dahrendorf et al. ... 128/202.26
4,879,996 A * 11/1989 Harwood, Jr. et al. .. 128/202.26
4,894,966 A * 1/1990 Bailey et al. ................. 52/317
5,029,578 A * 7/1991 Swiatosz ............... 128/202.26
5,036,841 A * 8/1991 Hamilton ............... 128/202.26
5,042,471 A * 8/1991 Drews et al. .......... 128/202.26
5,048,517 A * 9/1991 Pasterneck ............. 128/205.28

(List continued on next page.)

*Primary Examiner*—Aaron J. Lewis
*Assistant Examiner*—Mital Patel
(74) *Attorney, Agent, or Firm*—James G. Uber

(57) ABSTRACT

A closed circuit breathing apparatus comprising: a container containing a reactant for reacting with carbon dioxide and water to produce oxygen gas; a housing for the container; a foldable breathing bag and breathing tube assembly, including a mouthpiece disposed on the breathing bag, in gas-flow communication with the container; a cover for containing the folded breathing bag and breathing tube assembly; a strap for removably securing the cover onto the apparatus; and a chlorate candle for providing an initial volume of oxygen gas to the breathing bag wherein the breathing bag and breathing tube assembly is unfolded and the chlorate candle automatically fired by a user donning the mouthpiece.

20 Claims, 5 Drawing Sheets

U.S. PATENT DOCUMENTS 5,107,828 A * 4/1992 Koss et al. ............ 128/200.26
5,113,854 A 5/1992 Dosch et al.
5,222,479 A 6/1993 Brauer et al.
5,267,558 A * 12/1993 Haertle et al. ......... 128/202.26
5,301,665 A * 4/1994 Jumpertz et al. ...... 128/202.26
5,391,205 A * 2/1995 Knight .......................... 623/9
5,411,057 A * 5/1995 Pouchot ...................... 137/550
5,449,079 A * 9/1995 Yang .......................... 215/228
5,464,982 A 11/1995 Drucker et al.
5,529,312 A * 6/1996 Skinner et al. .............. 277/9.5
5,624,374 A * 4/1997 Von Iderstein ............... 600/29
5,653,223 A * 8/1997 Pruitt .................... 128/200.21
5,653,226 A * 8/1997 Heyer et al. ........... 128/202.26
5,690,099 A * 11/1997 Abramove et al. .... 128/202.26
5,797,521 A * 8/1998 Sobral ........................ 222/531
5,806,581 A * 9/1998 Haasch et al. ................ 165/76
5,876,039 A * 3/1999 Skinner et al. ............. 277/617

* cited by examiner

CLOSED CIRCUIT ESCAPE BREATHING APPARATUS

This application is a C-I-P of PCT/US97/15672 filed Sep. 5, 1997 and claims benefit of Prov. No. 60/025,617 filed Sep. 6, 1996.

FIELD OF THE INVENTION

The present invention relates in general to respiratory equipment and, in particular, to a combination breathing bag and breathing tube for a closed circuit escape breathing apparatus, also referred to as a Self-Contained Self-Rescuer (SCSR), wherein exhaled carbon dioxide and water vapor flow through and react with a chemical in a chemical cartridge to yield oxygen gas to be inhaled by the user.

BACKGROUND OF THE INVENTION

Closed circuit respirators or- SCSRs are known. The Portal-Pack™ self-contained self-rescuer made by the Mine Safety Appliances Company (MSA) of Pittsburgh, Pa. (see MSA Data Sheet No. 01-01-17) is an example of such a device. Other examples of closed circuit respirators are disclosed in U.S. Pat. No. 5,267,558 to Haertle, et al. and U.S. Pat. No. 4,459,981 to Mascher et al.

SUMMARY OF THE INVENTION

The present invention provides an SCSR which incorporates numerous improvements to produce an SCSR which is smaller, lighter, easier to use and maintain and more reliable than known SCSR devices.

The present invention provides an improved breathing bag/breathing tube assembly which allows for several improvements over known SCSR devices. Such improvements include the operational advantage of having the breathing bag automatically unfolded through the act of the user donning the mouthpiece. The breathing bag/breathing tube assembly further provides for the elimination of parts such as a storage plug for the mouthpiece and a voice transmission device. The design of the breathing bag/breathing tube assembly provides for the mouthpiece to be disposed on the breathing bag. This design enables the vent valve of the bag to act as a plug in the mouthpiece when the bag is folded for storage. The combination breathing bag/breathing tube also provides for a height reduction versus most known SCSR devices. Voice communication by the user is improved and the need for any voice transmission device eliminated since the breathing bag/breathing tube assembly acts as speaking amplification diaphragm.

The firing mechanism for the oxygen emitting candle is also automatically activated when the bag is unfolded by the user. The combination breathing bag/breathing tube also incorporates a curved, pleated metal mesh acting as a foldable heat exchanger which insures that the breathing tube remains open with a controllable low flow resistance and a comfortable breathing air temperature.

The main housing of the SCSR of the present invention defines a receptor which allows the SCSR to be quickly attached to and removed from the user's harness belt, thereby eliminating the cost and weight associated with fabric carrying pouches used in association with known SCSR devices. The projection which is received in the receptor to removably attach the SCSR to the harness belt is disposed on a mounting bracket which includes at least two means for removable mounting to a belt or a wall. A belt adaptor backing is also included for attaching the mounting bracket to various sizes of harness belts.

The SCSR of the present invention also utilizes a nose clip which requires only one hand to don or doff.

Other details and advantages of the present invention will become apparent from the following detailed description of the presently preferred embodiments of practicing the invention.

BRIEF DESCRIPTION OF THE DRAWINGS

The present invention is described with respect to the preferred physical embodiments constructed in accordance herewith. It will be apparent to those of ordinary skill in the art that various modifications and improvements may be made without departing from the scope and spirit of the invention. Accordingly, the invention is not limited by the specific embodiments illustrated and described, but only by the scope of the appended claims, including all equivalents thereof.

In the accompanying drawings, preferred embodiments of the invention and preferred methods of practicing the invention are illustrated in which.

DETAILED DESCRIPTION OF THE PREFERRED EMBODIMENTS

The present invention is described with respect to the preferred physical embodiments constructed in accordance herewith. It will be apparent to those of ordinary skill in the art that various modifications and improvements may be made without departing from the scope and spirit of the invention. Accordingly, the invention is not limited by the specific embodiments illustrated and described, but only by the scope of the appended claims, including all equivalents thereof.

Figure 1:
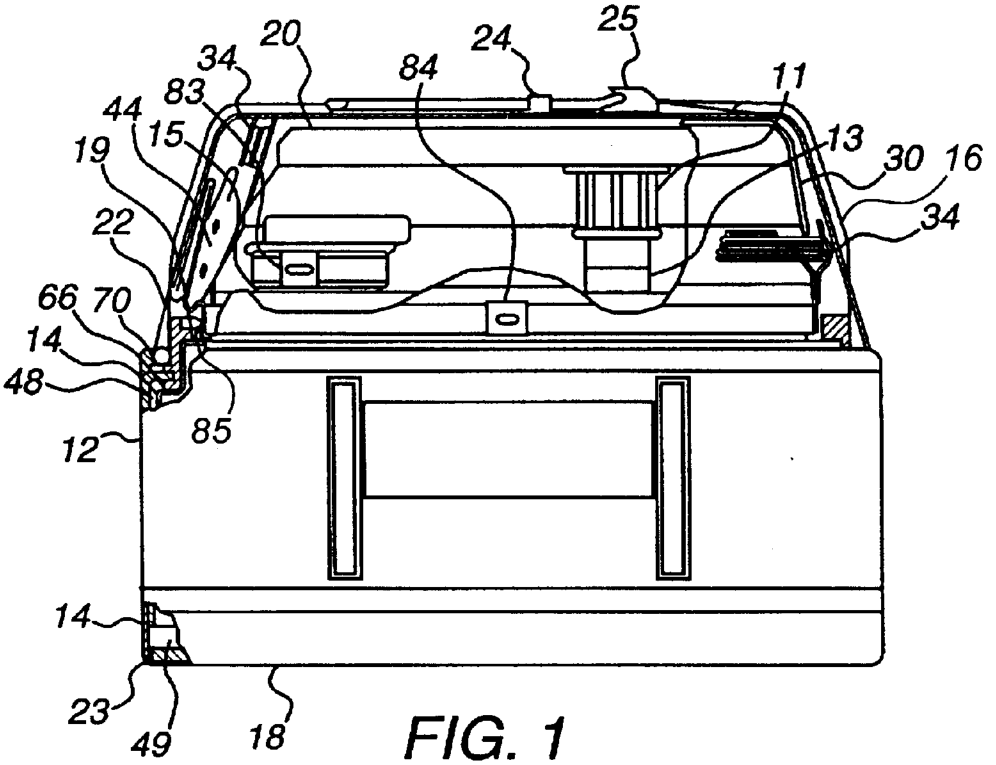
FIG. 1 is a front elevational view of a breathing apparatus of the present invention with the cover and housing partially cut away.
Figure 2:
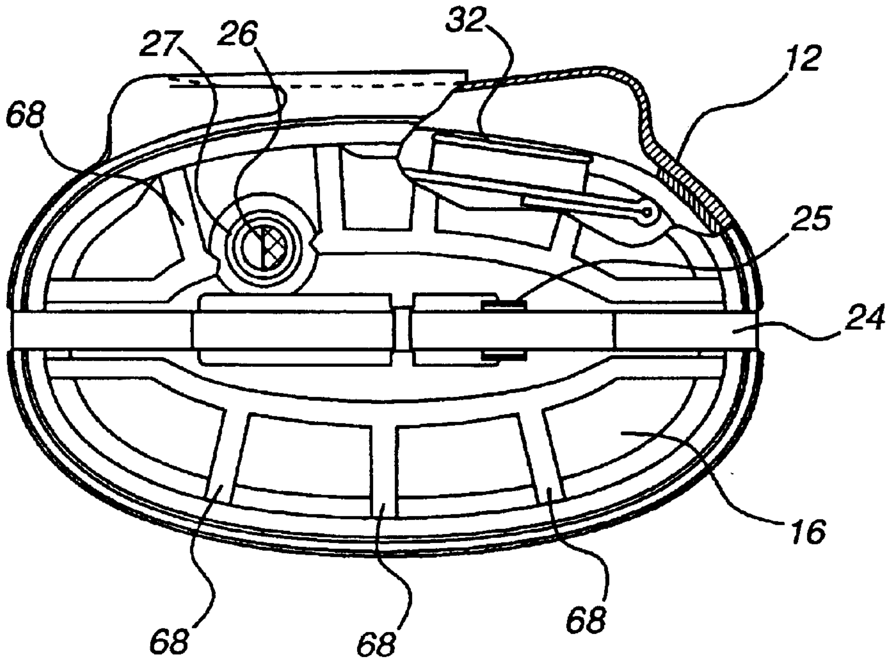
FIG. 2 is a top plan view of a breathing apparatus of the present invention with the cover and housing partially cut away.

As shown in FIGS. 1 and 2, a preferred embodiment of the closed circuit escape breathing apparatus 10 of the present invention comprises a main housing 12, preferably urethane, which houses the canister 14 and a top cover 16 which contains the combination breathing bag/breathing tube assembly 20 in its folded, storage position. The protective elastomeric top cap (not shown) and bottom cap 18 provide additional protection to the top cover 16 and canister 14, respectively, which are both preferably made of stainless steel. Ribs 68 are provided in the top cover 16 to increase the strength thereof.

A dual shock absorbing/sealing gasket 22 is disposed between the top cover 16 and the canister 14. An additional bottom shock absorbing gasket 23 is disposed between the bottom of the canister 14 and the elastomeric bottom cap 18. Air spaces 48 (vertical) and 49 (horizontal), respectively, are provided between the canister 14 and housing 12 to insulate the canister 14 during escape operation. A stainless steel band 24 and strap assembly 25 are used to secure the top cover 16 onto the canister 14 and thereby maintain a water tight seal therebetween. The elastomeric top cap is installed on the top cover 16 over the tightened steel band 24 and strap latch assembly 25 to protect the same from becoming unlocked inadvertently. The top cap will hold the band 24 in place if it becomes loose through rough handling. Also, the top cap absorbs shock if the SCSR 10 is bumped or dropped and hides dents in the cover 16 caused thereby.

The top mounted breathing bag and breathing tube assembly 20 requires only one water leakage indicator 26 which can be seen through a window 27 in the top cover 16. The elastomeric top cap also has a window through which the leakage indicator 26 can be viewed.

Figure 3:
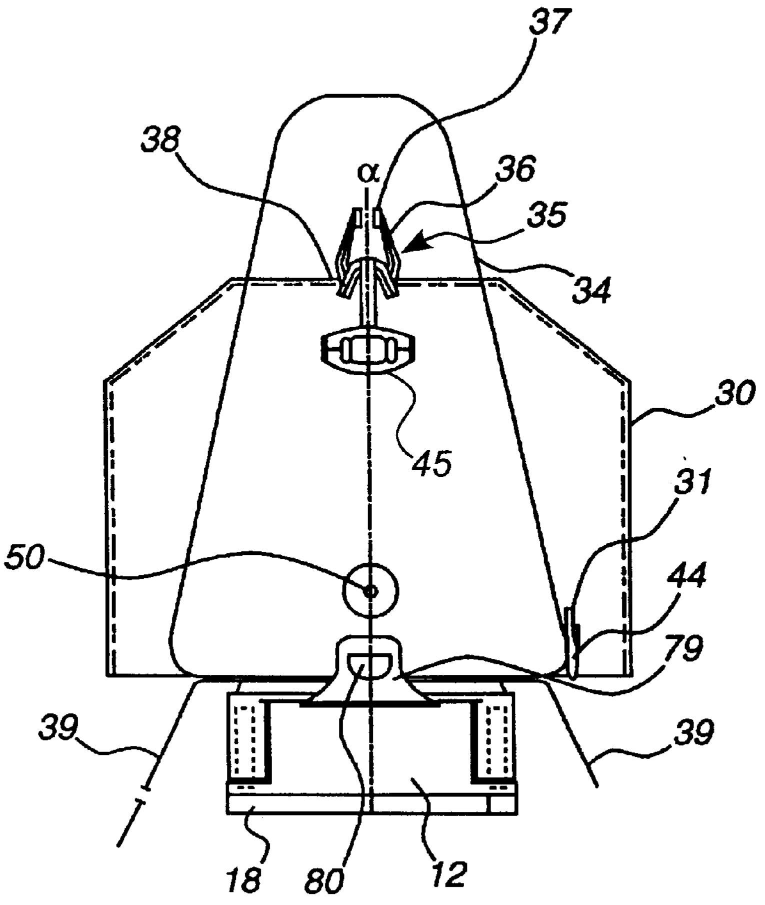
FIG. 3 is a rear elevational view of a breathing apparatus of the present invention with the breathing bag/breathing tube assembly in its unfolded, operational position.

FIG. 3 illustrates the combination breathing bag/breathing tube assembly 20 in its unfolded, operational position. The assembly 20 comprises the breathing bag 30, breathing tube 40, mouthpiece 45 and relief valve 50 disposed on the top of the canister 14 via breathing bag clamp 84. Having the assembly 20 disposed on the top of the canister 14 allows the breathing bag 30 to be worn in the protected area of the user's chest where the bag 30 is less likely to be bumped or perforated when the user crawls out of confined spaces. The top mounted breathing bag and breathing tube assembly 20 with the mouthpiece 45 disposed on the breathing bag 30 allows the bag 30 to function as a large speaking diaphragm, eliminating the need for separate voice transmission devices normally associated with known SCSR devices. The breathing bag 30, breathing tube 40 and mouthpiece 45 are preferably made from a relatively thin, flexible, incombustible and gas-impermeable material such as urethane plastic film.

Figure 6:
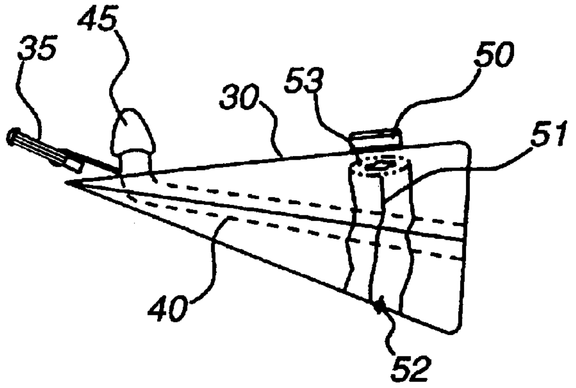
FIG. 6 is a side elevational, partial cut-away view of the breathing bag/breathing tube assembly of the present invention.
Figure 7:
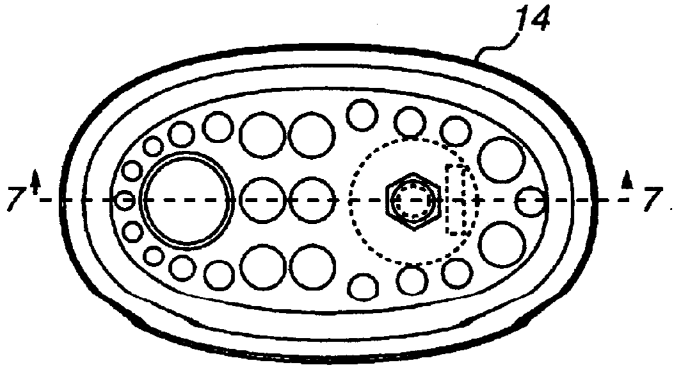
FIG. 7 is a top plan of the canister of the present invention.
Figure 8:
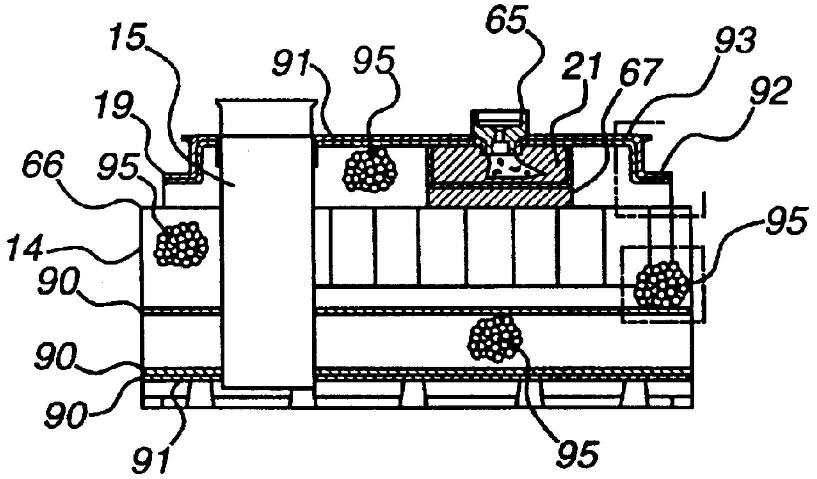
FIG. 8 is a cross-sectional view of the canister of the present invention along line 7—7 of FIG. 7.

As can be understood from FIGS. 3 and 6, the relief valve 50 can be inserted into the mouthpiece 45 when the breathing bag 30 is folded to be stored. This design eliminates the need for a separate plug for the mouthpiece 45, reducing the cost and the weight of the SCSR 10. In addition, plugs have generally been attached to the mouthpiece and would hit the user in the face during escapes. The plugless SCSR 10 of the present invention therefore embodies an improvement with respect to the operation of known SCSR devices.

Figure 4:
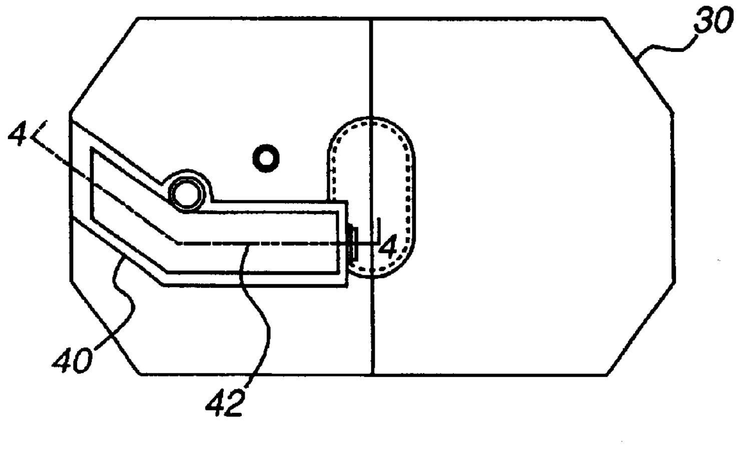
FIG. 4 is a top plan view of the breathing bag/breathing tube assembly of the present invention.
Figure 5:
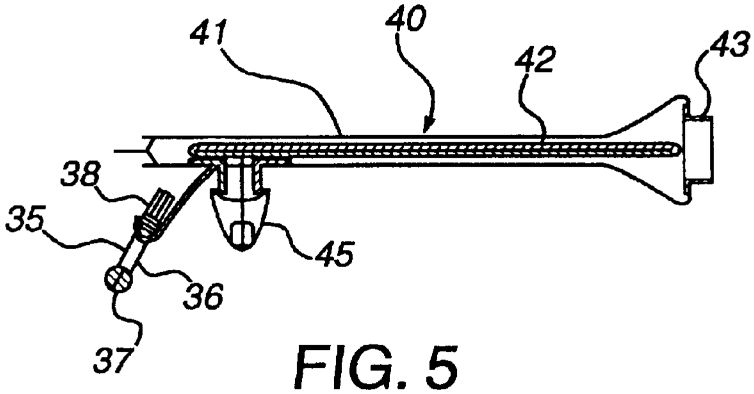
FIG. 5 is a cross-sectional view of the breathing tube of the present invention along line 4—4 of FIG. 4.

Another improvement embodied in the SCSR 10 of the present invention is the shape and construction of the breathing tube 40 which allows it to effectively house the metal mesh 42 heat exchanger and to be readily and compactly folded for storage. As is known, the oxygen liberating reaction between the reactant in the canister 14, preferably potassium superoxide ($KO_2$), and the carbon dioxide and water vapor exhaled by the user is highly exothermic. The gas from the breathing bag 30 and canister 14 must therefore be cooled prior to inhalation by the user. As shown in FIGS. 4 and 5, the breathing tube 40 comprises an outer sheath 41 which houses the pleated, metal mesh 42, woven as a continuous hinge and which is preferably made of copper.

The breathing tube 40 is curved or bent as shown in FIG. 4 to facilitate the ease of compactly folding the tube 40. The continuous hinge weave of the metal mesh 42 also facilitates the compact folding of the breathing tube 40, as well as the efficient extraction of heat from the air passing therethrough. The metal mesh 42 further supports the outer sheath 41, insuring that the breathing tube 40 remains open with a controllable, low flow resistance.

At its lower end, the breathing tube 40 defines a cylindrical connector 43 for attachment with the canister tube 15 via clamp 83. The mouthpiece 45 is attached or integrally formed with the upper end of the breathing tube and is disposed on the breathing bag 30 as shown in FIG. 6. The nose clip 35 is disposed on the mouthpiece 45. The nose clip 35 comprises a pair of arms 36, each arm having a nose pad 37 disposed on one end thereof. The arms 36 and nose pads 37 are biased towards each other by a compression spring such that little or no space exists between the nose pads 37. A scissor-type grip 38 can be squeezed with one hand to spread apart the nose pads 37 so that the nose clip 35 may be clamped onto the user's nose. The inside surfaces of the nose pads 37 are preferably roughened or scored in some manner so that the nose clip 35 does not easily slide off of oily or wet skin surfaces.

A neck strap 34 and a waist strap 39 are attached to the breathing bag 30 as shown in FIG. 3. The user is instructed to don the SCSR 10 by first placing the neck strap 34 over his head, and then adjusting the same only after the mouthpiece 45 and nose clip 35 are in place. This procedure ensures that the breathing bag is fully unfolded for the most effective operation of the SCSR 10.

A VELCRO® pad 31 is attached to the neck strap 34 which is used to secure goggles 32 within the protected environment of the top cover 16. In this manner, the goggles 32 are readily accessible and do not get lost in the process of donning the SCSR 10.

To prevent the breathing bag 30 from over filling, the relief valve 50 is constructed to open after the bag 30 has been filled to a predetermined volume. As seen in FIG. 6, a relief strap 51 is attached by a rivet 52 or by other known means to the side wall of the breathing bag 30 opposite the relief valve 50. The relief strap 51 is also attached to the spring-biased valve element 53 of the relief valve 50 such that when the breathing bag 30 is filled beyond the predetermined volume, the relief strap 51 pulls the valve element 53 to its open position to release gas from the breathing bag 30. After enough gas escapes to reduce the volume in the breathing bag 40 below the predetermined volume, the spring-biased element 53 closes the relief valve 50.

Figure 9:
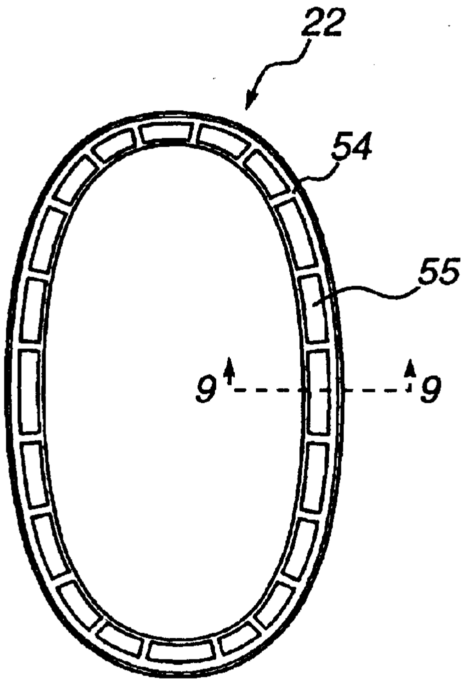
FIG. 9 is a top plan view of the annular elastomeric gasket of the present invention.
Figure 10:
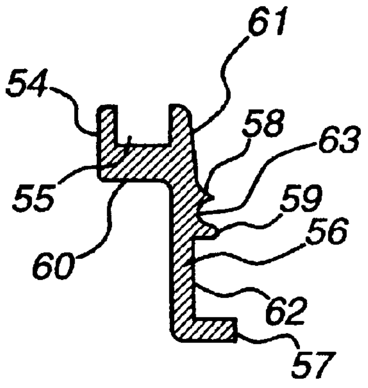
FIG. 10 is a cross-sectional view of the annular elastomeric gasket of the present invention along line 9—9 of FIG. 9.

As shown in FIGS. 1, 9 and 10, the elastomeric gasket 22 comprises an upper, annular portion 54 which defines a plurality of circumferentially spaced, generally rectangular openings 55. The annular portion 54 is integrally formed with the annular wall 56 which terminates in an annular foot 57. First and second annular ribs 58 and 59, respectively, are defined by the outer surface of the annular wall 56 and are spaced from the annular foot 57 as shown in FIG. 10. The gasket 22 is disposed both between the top cover 16 and the canister 14 and between the main housing 12 and the canister 14.

As shown in FIG. 1, the upper annular portion 54 is disposed between the inside of top cover 16 and the canister 14. More specifically, the bottom 60 of the upper annular portion 54 is disposed on a first upper annular shoulder 19 of the canister 14. The openings 55 allow the upper annular portion 54 to absorb more energy transmitted through the cover 16 upon the SCSR 10 being bumped or dropped compared to a solid elastomeric gasket. The outer surface 61 of the upper annular portion 54 and the outer surface 62 of annular wall 56 provide sealing surfaces which act against the inside of top cover 16 to prevent the entry of water vapor and other foreign substances into the SCSR 10. Additional sealing surfaces are provided by the annular ribs 58 and 59 which are compressed against each other by the top cover 16 when it is secured onto the canister 14 by the band 24. Prior to installation of the top cover 16, silicone grease is preferably applied around the entire circumferential surface of annular groove 63 to prevent the annular ribs 58 and 59 from bonding to the stainless steel top cover 16 over long storage periods. The silicone grease also enhances the watertight seal provided by the gasket 22.

The annular foot 57 also acts to absorb energy transmitted through the main housing 12 to protect the canister 14. The annular foot 57 is preferably disposed on a second upper annular shoulder 66 defined by the canister 14 and interlocked with an inward annular flange 70 defined by the main housing 12.

Figure 11:
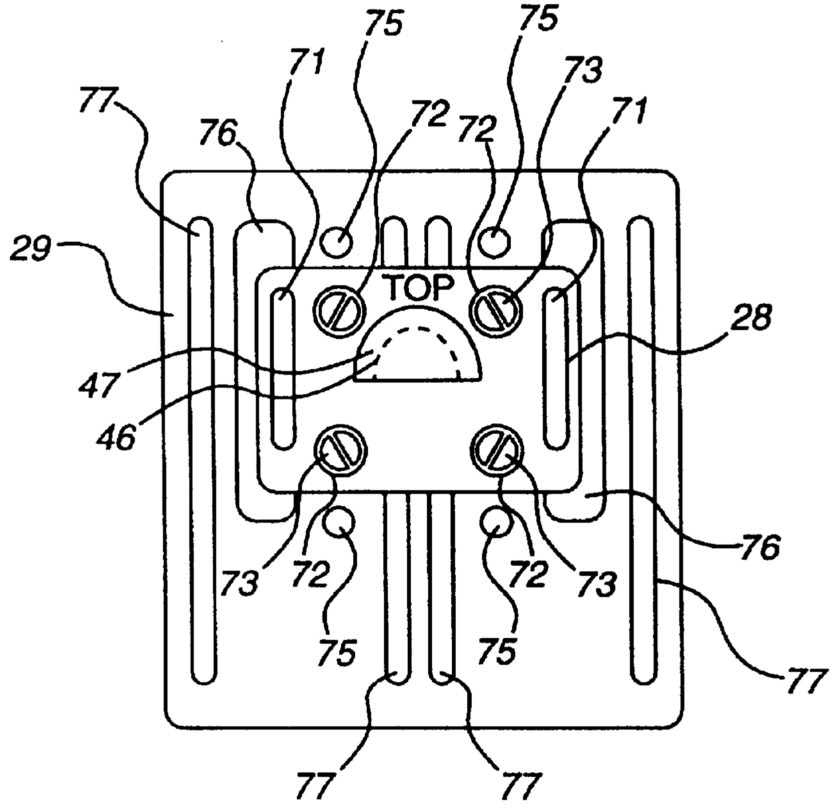
FIG. 11 is a front elevational view of the mounting bracket and adapter plate of the breathing apparatus of the present invention.

Referring to FIG. 11, shown therein are the mounting bracket 28 and the adapter plate 29. A projection 46 having a semi-circular face plate 47 is disposed on the mounting bracket 28 which may be attached to a harness belt in various ways. The mounting bracket 28 defines two elongated slots 71 through which the bracket 28 may be attached to a one-inch wide belt. The mounting bracket 28 also defines a plurality of apertures 72 for receiving fasteners such as screws 73 or rivets (not shown) for removably securing the bracket 28 directly to harness belts of various other sizes or to a wall or other mounting surfaces.

The mounting bracket 28 may also be removably attached by screws 73 to the adapter plate 29 to provide yet additional options for attaching the mounting bracket 28 to other sizes and styles of harness belts. The adapter plate 29 defines a plurality of apertures 75, wide slots 76 and narrow slots 77 for such purpose. After the mounting bracket 28 has been secured to a harness belt or other surface upon which the SCSR is to be removably mounted, the semi-circular receptor aperture 80 defined by the upwardly extending tab 79 of the main housing 12 (see FIG. 3) is matingly oriented with face plate 47. After the projection 46 and face plate 47 have been inserted into the aperture 80, the SCSR 10 is rotated 180 degrees to removably lock the SCSR 10 onto the mounting bracket 28.

The above-described means for mounting the SCSR 10 comprising the mounting bracket 28, projection 46 with face plate 47 and the receptor aperture 80 defined by the tab 79 of the main housing 12 allows the SCSR 10 to be directly and securely removably mounted to the user's harness belt or to a wall or other flat surface for storage. The need for less effective carry pouches, which do not hold the SCSR as securely to the belt such that it dangles or droops from the user's side, is eliminated. The attachment means of the present invention also allows for the SCSR 10 to be removed more quickly from a harness belt or other mounting surface so that the user can activate the device more expediently before the surrounding environment becomes totally devoid of breathable air. Other advantages include the cost savings and weight reduction associated with the elimination of fabric carry pouches.

To operate the SCSR 10, the user removes the elastomeric top cap and unfastens the strap assembly 25 to remove the stainless steel band 24 holding the top cover 16 onto the canister 14. As shown in FIG. 1, the band 24 includes a hook 85 that is engaged with the underside of the rim of the top cover 16.

The hook 85 together with the steel band 24 act as a lever for prying off the top cover 16 in situations where, due to changes in temperature and/or atmospheric pressure, vacuum or pressure forces operate to hold the top cover 16 onto-the canister 14. Thus, the user can use the hook 85, if necessary, to quickly remove the top cover 16.

The user is next instructed to loop the neck strap 34 over his head and to don the mouthpiece 45 and clamp the nose clip 35 onto his nose to seal both nostrils. Performing these acts first automatically ensures that the breathing bag 30 is completely unfolded and extended to its full length thereby providing the most effective operation of the SCSR 10. The user can then put on the goggles 32 and adjust the neck strap 34 via neck strap adjuster 44 so that there is no weight on the mouthpiece 45. The waist strap 39 is then wrapped around the torso and tied in a shoe-string knot to secure the SCSR 10 on the body.

Figure 12:
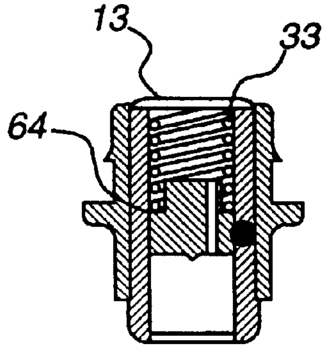
FIG. 12 is a cross-sectional view of the firing mechanism of the present invention.

The initial volume of oxygen which fills the breathing bag 30 is supplied by the burning of a chlorate candle 21 in candle assembly 67 which is automatically fired by firing mechanism 13 when the breathing bag 30 is unfolded. A coupling/activator 11 attached to both the breathing bag 30 and to the firing mechanism 13 automatically activates the firing mechanism 13 when the bag 30 is unfolded. The breathing bag 30 unfolding motion only has to move the coupling 11 less than one quarter of an inch with minimal force to activate the firing mechanism 13. When activated, the firing mechanism 13 (FIG. 12) transfers the potential energy of spring 33 into kinetic energy of the plunger 64 which impacts and ignites a primer in primer assembly 65 which in turn ignites the candle 21. Thus, the construction of the SCSR 10 of the present invention wherein the mouthpiece 45 is disposed on the breathing bag 30 provides for the complete unfolding of the breathing bag 30 and for the automatic activation of the candle firing mechanism 13 when the user dons the mouthpiece 45.

Preferably, the SCSR 10 of the present invention employs a CHEMOX quick start candle 21 which supplies the initial ten liter volume of oxygen to the breathing bag 30 in about 30–60 seconds. If the candle does not automatically fire during the donning process, the user must breath ambient air and exhale 10 to 15 times into the breathing tube 40 to activate the $KO_2$ in the canister 14.

The hot oxygen coming from the candle 21 is exhausted first into the center of the canister 14 to warm the chemical, preferably potassium superoxide ($KO_2$), in cold environments. The initial supply of oxygen from the candle allows the potassium superoxide 95 to become activated as the user breathes the oxygen and exhales into the SCSR 10. When the user exhales, the carbon dioxide ($CO_2$) and water vapor travel through the breathing tube 40 into the canister tube 15 to the bottom of the canister 14. The exhaled air then rises into the beds of potassium superoxide 95 in the canister 14, up through the separator screens 90 (preferably number six mesh steel, copper flashed), filters 91, a lower screen 92 and an upper screen 93 disposed in the canister 14 and then into the breathing bag 30. The bottom plerum acts to trap saliva and keep it separated from the potassium superoxide in the canister 14.

The $CO_2$ and water vapor react with the $KO_2$ in the canister 14 to produce oxygen gas and to remove $CO_2$ from the breathable gas. The SCSR 10 of the present invention is a pendulum or double pass SCSR wherein the air breathed in from the breathing bag 30 passes twice through the $KO_2$ in the canister 14 before being inhaled. The exhaled air, that is, passes through the $KO_2$ in the canister 14 on its way into the breathing bag 30 and again on its way from the breathing bag 30 to the user's mouth.

Although the invention has been described in detail in the foregoing for the purpose of illustration, it is to be understood that such detail is solely for that purpose and that variations can be made therein by those of ordinary skill in the art without departing from the spirit and scope of the invention as defined by the following claims, including all equivalents thereof.

What is claimed is:

1. A closed circuit breathing apparatus comprising:

a container containing a reactant for reacting with carbon dioxide and water to produce oxygen gas;

a housing for the container;

a breathing bag and a breathing tube in gas-flow communication with the container;

a mouthpiece in gas-flow communication with the breathing tube;

a cover for containing the breathing bag, the breathing tube and the mouthpiece;

means for removably securing the-cover onto the apparatus; and an annular gasket comprising an upper annular portion, an annular wall and an annular foot wherein the upper annular portion and the annular wall are disposed between the cover and the container and the annular foot is disposed between the housing and the container.

2. The breathing apparatus of claim 1 wherein the housing defines an inner annular flange disposed between first and second annular shoulders defined by the container and wherein the upper annular portion of the annular gasket is disposed on the first annular shoulder and the annular foot is disposed on the second annular shoulder.

3. The breathing apparatus of claim 1 wherein the upper annular portion of the annular gasket defines a plurality of circumferentially spaced openings.

4. The breathing apparatus of claim 1 wherein the breathing tube defines a non-linear shape and houses a mesh material for absorbing heat from the air to be inhaled by a user of the apparatus.

5. The breathing apparatus of claim 4 wherein the mesh material is copper.

6. The breathing apparatus of claim 4 wherein the mesh material is woven as a continuous hinge to facilitate folding of the breathing tube and breathing bag for storage within the cover.

7. The breathing apparatus of claim 1 wherein the means for removably securing the cover onto the apparatus comprises a band, band latching mechanism and a hook disposed, at least in part, between the gasket and the cover when the cover is removably secured to the apparatus.

8. The breathing apparatus of claim 1 wherein the means for removably mounting comprise a semi-circular aperture defined by the housing, a mounting bracket comprising a planar surface having a projection disposed thereon, the projection having a first end defining a semi-circular face, the planar surface defining at least two spaced-apart slots.

9. The breathing apparatus of claim 8 wherein the planar surface of the mounting bracket further defines a plurality of apertures.

10. The breathing apparatus of claim 9 wherein the means for removably mounting further comprises an adapter plate defining at least one pair of spaced apart slots and a plurality of apertures for receiving fasteners for attaching the adapter plate to the mounting bracket.

11. A closed circuit breathing apparatus comprising:

a container containing a reactant for reacting with carbon dioxide and water to produce oxygen gas;

a housing for the container;

a foldable breathing bag and breathing tube assembly, including a mouthpiece disposed on the breathing bag, in gas-flow communication with the container;

a cover for containing the folded breathing bag and breathing tube assembly;

means for removably securing the cover onto the apparatus; and means for providing an initial volume of oxygen gas to the breathing bag wherein the breathing bag and breathing tube assembly is unfolded and the means for providing oxygen gas are activated by a user donning the mouthpiece.

12. The breathing apparatus of claim 11 wherein the breathing tube is disposed completely within the breathing bag.

13. The breathing apparatus of claim 11 further comprising an annular gasket comprising an upper annular portion, an annular wall and an annular foot wherein the upper annular portion and the annular wall are disposed between the cover and the container and the annular foot is disposed between the housing and the container.

14. The breathing apparatus of claim 13 wherein the housing defines an inner annular flange disposed between first and second annular shoulders defined by the container and wherein the upper annular portion of the annular gasket is disposed on the first annular shoulder and the annular foot is disposed on the second annular shoulder.

15. The breathing apparatus of claim 19 wherein the upper annular portion of the annular gasket defines a plurality of circumferentially spaced openings.

16. The breathing apparatus of claim 19 wherein the means for removably securing the cover onto the apparatus comprises a band, band latching mechanism and a hook disposed, at least in part, between the gasket and the cover when the cover is removably secured to the apparatus.

17. The breathing apparatus of claim 11 wherein the breathing tube defines a non-linear shape and houses a mesh material for absorbing heat from the air to be breathed by a user of the apparatus.

18. The breathing apparatus of claim 17 wherein the mesh material is copper.

19. The breathing apparatus of claim 17 wherein the mesh material is woven as a continuous hinge to facilitate folding of the breathing tube and breathing bag assembly for storage within the cover.

20. The breathing apparatus of claim 17 wherein the housing defines a semi-circular aperture for removably receiving a projection with a semi-circular face to removably mount the breathing apparatus.

* * * * *